United States Patent
Eguchi et al.

(10) Patent No.: US 6,783,363 B2
(45) Date of Patent: Aug. 31, 2004

(54) DISCOLORED TEETH BLEACHING SYSTEM

(75) Inventors: Hiromasa Eguchi, Hyogo (JP); Kazutomo Takami, Kanagawa (JP); Takuro Ishibashi, Nagasaki (JP); Toru Nonami, c/o AIST Chubu Nat'l Inst. of Adv. Ind Sci. and Tec. 2266-98, Anagahora, Shimo-Shidami, Moriyama-ku, Nogoya-shi, Aichi (JP), 463-8560

(73) Assignees: Ushio Denki Kabushiki Kaisya, Tokyo (JP); EVIS Inc, Shimoagata-gun (JP); Toru Nonami, Nagoya (JP); National Institute of Advanced Industrial Science and Technology, Tokyo (JP)

( * ) Notice: Subject to any disclaimer, the term of this patent is extended or adjusted under 35 U.S.C. 154(b) by 127 days.

(21) Appl. No.: 10/109,868

(22) Filed: Apr. 1, 2002

(65) Prior Publication Data

US 2002/0177097 A1 Nov. 28, 2002

(30) Foreign Application Priority Data

Mar. 30, 2001 (JP) ........................................ 2001-101967

(51) Int. Cl.[7] .................................................. A61C 3/00
(52) U.S. Cl. ........................................ 433/29; 433/215
(58) Field of Search ................................... 433/29, 215

(56) References Cited

U.S. PATENT DOCUMENTS

| | | | |
|---|---|---|---|
| 4,661,070 A | * | 4/1987 | Friedman ..................... 433/215 |
| 5,098,303 A | | 3/1992 | Fischer ....................... 433/215 |
| 6,231,343 B1 | | 5/2001 | Ishibashi et al. ............. 433/215 |
| 6,439,888 B1 | * | 8/2002 | Boutoussov et al. ........ 433/215 |

FOREIGN PATENT DOCUMENTS

| | | |
|---|---|---|
| JP | 5-320033 | 12/1993 |
| JP | 8-143436 | 6/1996 |

* cited by examiner

*Primary Examiner*—John J Wilson
(74) *Attorney, Agent, or Firm*—Oblon, Spivak, McClelland, Maier & Neustadt, P.C.

(57) ABSTRACT

A system for bleaching discolored teeth is provided, and this system has a function irradiating light emitted from a light-emitting section to the surface of teeth applied with a chemical agent including titanium dioxide and hydrogen peroxide, a irradiation energy of wavelength 380 to 420 nm of the light emitted from the light-emitting section is at least 37 mW/cm$^2$ and the ratio of irradiation energy of wavelength 380 to 420 nm with respect to the irradiation energy of wavelength 200 to 800 nm thereof is at least 36% at this light-emitting section, and whereby it is possible to obtain high bleaching effect of the teeth, to reduce the heat applied to the teeth to a low level (no more than 40° C.) and to reduce emission of ultraviolet light that has an adverse effect on the human body to a low level.

4 Claims, 9 Drawing Sheets

DISCOLORED TEETH BLEACHING SYSTEM

BACKGROUND OF THE INVENTION

1. Field of the Invention

The present invention relates to a system for bleaching discolored teeth, used for bleaching pigments (coloration, discoloration) deposited on teeth, and more particularly, it relates to a system for bleaching discolored teeth, having a function of irradiating with light for bleaching teeth by a photocatalytic action, wherein a chemical agent comprising titanium dioxide and aqueous hydrogen peroxide is applied to the surface of the teeth and these are irradiated with the light.

2. Description of the Related Art

In recent years, in dental therapy, demands for so-called cosmetic improvements, in which the contour, alignment and integrity etc of the teeth are improved are increasing. Of these, recently, cases in which young women are seeking dental therapy with a view to whitening the teeth, as an important element in facial beauty, are increasing. Causes of dental discoloration or pigmentation/staining may be generally divided into so-called extrinsic causes such as for example deposition of colored substances (tobacco, tea stains and the like), pigment-generating bacteria, discoloration of repair materials (chiefly composite resin), or metallic salts (chiefly amalgam, silver nitrate, or ammonia silver) and so-called intrinsic causes such as for example aging, chemical substances or chemical agents (fluorine, tetracycline and the like), dysmetabolism or hereditary diseases, or dental injuries; however, in dental health therapy, the chief applications of the bleaching method are in the latter i.e. intrinsic cases, where there is dental discoloration of pulpless teeth.

Several methods have been proposed in the past as methods for the cosmetic improvement of discolored teeth, among which bleaching may be considered a highly effective method for the preservation of dentine, despite drawbacks such as occasional recurrence, when methods suited to individual cases are selected and properly carried out.

Bleaching is essentially a method for decolorizing colored substances by means of a chemical reaction. In the past there have been various reports of bleaching agents comprising a variety of chemical agents based on vital bleaches and non-vital bleaches, as well as bleaching methods involving the use of such agents.

The following are some typical examples.

1) Methods of bleaching using 30% $H_2O_2$ as the chemical agent, with combined use of light and heat on the aqueous hydrogen peroxide.
2) Bleaching using 30% $H_2O_2$ as the chemical agent, and the concurrent use of high frequency current on the aqueous hydrogen peroxide.
3) Bleaching in which a paste comprising Aerosil (silica fine powder) mixed with 35% $H_2O_2$ is used as the chemical agent, and the aqueous hydrogen peroxide and Aerosil paste is applied.
4) Bleaching in which a paste obtained by kneading a 35% $H_2O_2$ solution and a powder (ingredients comprising potassium sulfate, manganese sulfate, silicon dioxide, or the like) is used as the chemical agent (MATSUKAZE HIGHLIGHT, Trademark).
5) Bleaching in which a mixture of 1 mL of 30% HCl, 1 mL of 30% $H_2O_2$, and 0.2 mL of diethyl ether is used as the chemical agent (improved MacInnes bleaching).
6) A method in which a kneaded paste of 30% $H_2O_2$ and a sodium perborate powder is used as the chemical agent (working bleach method).

Many other bleaching methods have also been reported, such as the dental bleaching agent and method comprising a mixture of aqueous hydrogen peroxide and ortho-phosphoric acid (Japanese Laid-Open Patent Publication No. H8-143436/1996), the bleaching agent comprising a mixture of silicic anhydride with aqueous hydrogen peroxide, and the vital bleaching method comprising the application of such a bleaching agent (Japanese Laid-Open Patent Publication No. H5-320033/1993), and the dental bleaching composition comprising a dental bleaching agent (such as hydrogen-urea peroxide, hydrogen peroxide-carbamide, and carbamide peroxide) and a matrix material (such as carboxymethylene), a method for bleaching teeth using the above (Japanese Laid-Open Patent Publication No. H8-113520/1996) and a method for bleaching discolored teeth using photocatalysis of titanium dioxide (published Japanese Patent No. 3030380/2000).

As can be seen from the foregoing prior art, a technique is known to perform bleaching of pigment deposited on teeth (coloration, discoloration) by combining irradiation with light with a chemical agent based on titanium dioxide and aqueous hydrogen peroxide. For example, in the above Japanese Patent publication No. 3030380, regarding the irradiation with light, it is merely stated that, although it is desirable to perform the irradiation with high-energy ultra-violet light, from the point of view of generating activated oxygen by the photocatalytic effect and from the point of view of its oxidative action, since ultraviolet light affects the human body, it is desirable to perform irradiation with violet light. However, what kind of light is actually effective is not known, and the details thereof are not known.

Also, the bleaching function changes considerably depending on the concentration of the aqueous hydrogen peroxide. When aqueous hydrogen peroxide is introduced into the mouth, in the case of aqueous hydrogen peroxide of high concentration, there is an adverse effect on the human body and in recent years, in accordance with various tests, from the point of view of both bleaching and safety, the concentration of aqueous hydrogen peroxide is determined as 3%.

However, the optimum conditions for light and chemical agents including 3% aqueous hydrogen peroxide have not been discovered; for example, even if a specific type of light has a bleaching function, heat is also generated by irradiation with light, so that the tooth crown is heated whilst bleaching, causing inflammation of the pulp; or there was the problem of emission of ultraviolet light, which has an adverse effect on the human body.

SUMMARY OF THE INVENTION

The present invention has been made in view of the above, its object is to provide a system for bleaching discolored teeth, wherein, when bleaching teeth using a chemical agent comprising titanium dioxide and aqueous hydrogen peroxide, reliable bleaching of the teeth can be achieved, yet little heat is applied to the teeth and essentially no ultraviolet light that has an adverse effect on the human body is irradiated.

Briefly, this object and other objects of the present invention as hereinafter will become more readily apparent can be attained by an apparatus for bleaching discolored teeth, which comprises:

a light source, a mirror for condensing the light from said light source, a wavelength cut-off filter and a light-emitting section, wherein the light emitted from the light-emitting section having a wavelength of 800 nm or higher is cut from the spectrum of light emitted by the light-emitting section by the wavelength cut-off filter, the radiant energy of light of the wavelength range of 380 to 420 nm is at least 37 mW/cm$^2$, and the ratio of light of the wavelength range of 380 to 420 nm to light of the wavelength range of 200 to 800 nm is at least 36% of the light emitted from the light-emitting section.

DESCRIPTION OF THE PREFERRED EMBODIMENTS

Next, the present invention is further described in detail.

As described above, in the system according to the present invention, the light emitted from the light-emitting section satisfies the following conditions:

light with a wavelength of 800 nm or higher is cut by the wavelength cut off filter, the irradiation energy of 380 to 420 nm thereof is at least 37 mW/cm$^2$ and the ratio of irradiation energy of 380 to 420 nm with respect to the irradiation energy of 200 to 800 nm thereof is at least 36% at the light-emitting section.

The system for bleaching discolored teeth of the present invention has the function of directing light emitted from the light source to light-emitting section by the light-guide member, and irradiating the light onto the surface of teeth applied with a chemical agent comprising titanium dioxide and aqueous hydrogen peroxide; it has the capability of completing bleaching of the teeth in about five minutes.

The ability to complete bleaching in five minutes is a very important factor in implementing an optical irradiation system, since, normally, it is difficult for a patient receiving treatment to maintain the mouth in an open condition for more than five minutes.

Figure 1:
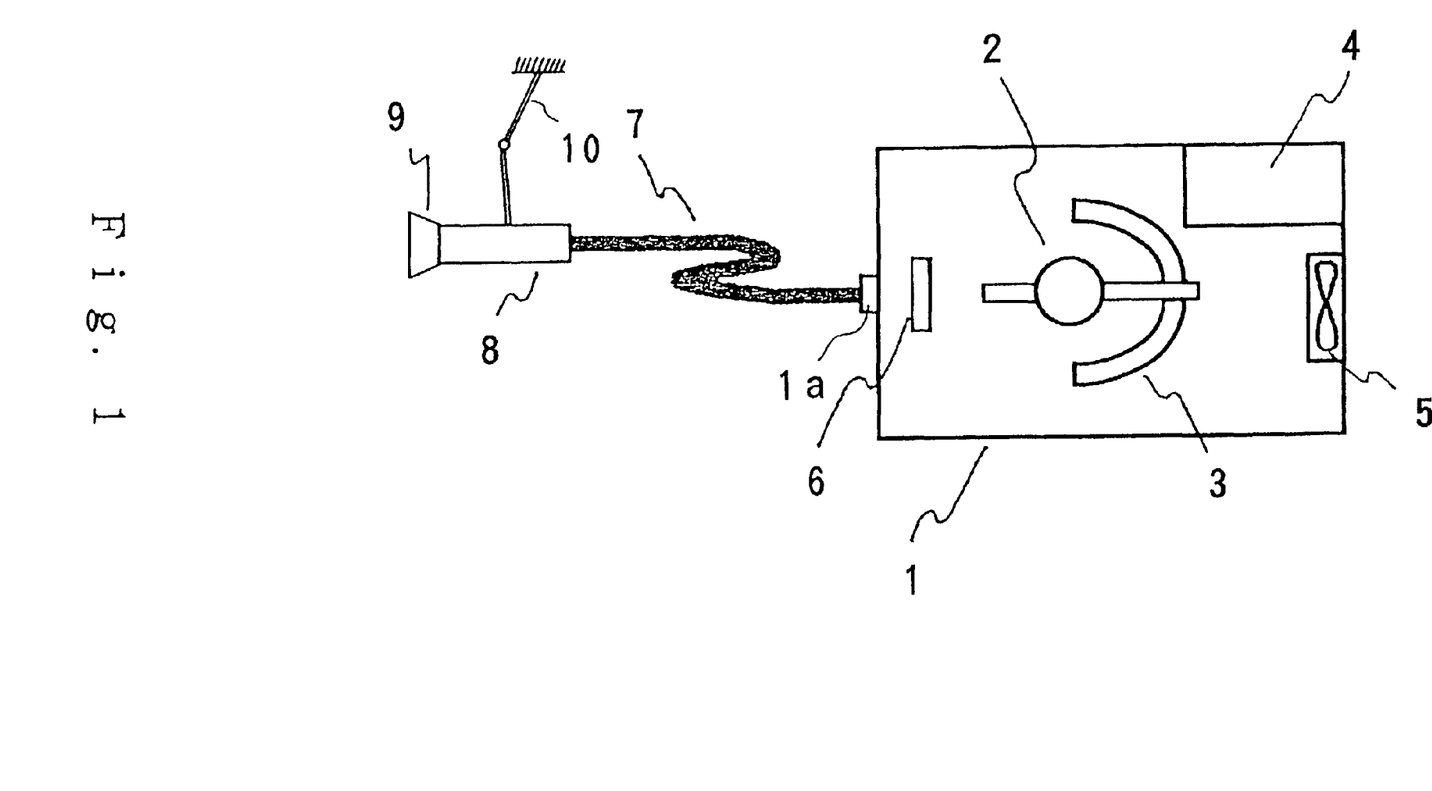
FIG. 1 is a diagram of a system for bleaching discolored teeth according to an embodiment of the present invention.

FIG. 1 shows an example of the construction of a system for bleaching discolored teeth according to the present invention.

In FIG. 1, 1 is a light device, 2 is a light source (lamp), 3 is a mirror, 4 is a power source, 5 is a cooling fan, 6 is a wavelength cut-off filter, 7 is a light-guide member, 8 is a light-guide, 9 is a light-emitting section and 10 is a holder, 1a indicates a light-emitting section of the light device that emits light passing through a wavelength cut-off filter formed on the light device 1.

In the system as described above, preferably a meta-hala (metal halide lamp) or halogen (halogen incandescent lamp) is employed as the light source (lamp). As the wavelength cut-off filter, a single or a plurality of filters may be employed, for example, an infrared cut-off filter that cuts off wavelengths of 800 nm or more, a cold filter that passes wavelengths of the region 200 to 450 nm, a blue filter that passes wavelengths centered on 400 nm or a wavelength selection filter that passes wavelengths of the region 380 to 420 nm but does not pass other wavelengths or the like. Also, as a light-guide member, preferably an optical fiber may be employed.

The light emitted from light source 2 is collected by mirror 3 and adjusted to light of a specified wavelength region by a single or a variety of wavelength cut-off filters 6, and is directed to light-emitting section 9 through light-guide member 7 and light-guide 8, and is irradiated onto the surface of the teeth through this light-emitting section 9.

The light emitted from light-emitting section 9 in the system described above must satisfy the following conditions.

The light emitted from light-emitting section 9 must have a condition 1 that a irradiation energy of wavelength 380 to 420 nm of the light is at least 37 mW/cm$^2$.

This condition is determined taking into account the fact that a chemical agent comprising titanium dioxide and aqueous hydrogen peroxide has an excellent bleaching effect in the wavelength region of 380 to 420 nm, the fact that, when the emitted energy is less than 37 mW/cm$^2$, the energy is small so that a very long time is taken to achieve bleaching, which means that the patient undergoing treatment must keep his mouth open for at least 5 minutes, and that, when the emitted energy is at least 37 mW, a reliable bleaching effect can be expected within 5 minutes.

The light emitted from light-emitting section 9 must have a condition 2 is that the ratio of the irradiation energy at 380 to 420 nm with respect to the irradiation energy of wavelength 200 to 800 nm is at least 36%.

This condition is determined with a view to reducing the amount of light on the long wavelength side, which constitutes heat energy, and to achieving efficient irradiation with light in the wavelength region 380 to 420 nm, which contributes to the bleaching effect.

Preferably the ratio of irradiation energy of 380 nm or less is no more than 5% with respect to the irradiation energy of wavelength 200 to 800 nm.

This is in order to reduce the amount of ultraviolet radiation, which has an adverse effect on the human body. It is believed that there are no adverse effects on the human body so long as the ratio of irradiation energy of no more than 380 nm is no more than 5%.

Although condition 1 and condition 2 described above were explained with reference to light emitted from light-emitting section 9, if no light guide member 7 is required, a light device of the light-emitting section 1a of the light device 1 has the same role and function as light-emitting section 9 described above. In this case, the light emitted from the light device of the light-emitting section 1a is directly incident on the surface of the teeth, so it must satisfy condition 1 and condition 2 above.

That is, as shown in FIG. 1, with regard to the light-emitting section in the invention of the present application, if a light-guide member 7 is provided, the light emitting section is light-emitting section 9, but if light-guide member 7 is not required, the light emitting section is light device of the light-emitting section 1a.

In the present invention, a chemical agent comprising titanium dioxide and hydrogen peroxide is employed, but, as a preferable aspect thereof, there may be mentioned by way of example a chemical agent consisting of a solution/paste of titanium dioxide powder and aqueous hydrogen peroxide of low concentration (preferably, no more than 6%). In this case, as the titanium dioxide, for example, titanium dioxide of particle size about 5 to 60 nm, in particular, titanium dioxide fine particles of the anatase type or material consisting chiefly thereof may be preferably employed, but there is no restriction to these and any material having the same effects as these may be employed in the same way irrespective of its form or shape. Material of small particle size is particularly preferred since it has the advantages that high photocatalytic activity can be expected, the amount to be deposited on the teeth need only be small, the amount to be used can be reduced, and, since the applied film is thin, for example, a high bleaching effect is obtained in a short time (within five minutes).

The ratios of the amounts of the above constituents can be preferably altered and adjusted for example for the cases of light discoloration and severe discoloration and in this way a range of products can be prepared preferable for various cases.

The chemical agent used in the present invention is employed in the form of a uniform transparent solution or paste by blending, kneading and dispersing fine titanium dioxide powder in low-concentration aqueous hydrogen peroxide, but there is no restriction to these and preparations obtained in the same way as these could be likewise employed. There is no particular restriction regarding the preparation means or device and the like for the chemical agent and preferable means or devices may be employed. In the present invention, application of the chemical agent to the surface of the teeth means coating and depositing this chemical agent onto the surface of the teeth, there being no particular restriction regarding the coating means. Furthermore, although, in the present invention, normally, the above chemical agent is employed in a form in which the above two constituents are used together as active constituents, it would be possible for these constituents to be prepared separately and combined when used.

In the present invention, light emitted from the light-emitting section of a system according to the present invention is directed onto the surface of teeth applied with the aforesaid chemical agent, wherein application of the chemical agent to the surface of the teeth and irradiation with light to the teeth could be performed once or repeated a few times. The extent and the number of times of application of this chemical agent and irradiation with light can be preferably adjusted in accordance with the degree of severity of the discoloration of the teeth.

The chief function of the chemical agent comprising titanium dioxide and hydrogen peroxide employed in the present invention and irradiation with light using the system of the present invention is a bleaching function produced by the synergetic effect of photocatalytic activation of the titanium dioxide by irradiation with light and the bleaching function produced by the aqueous hydrogen peroxide of low concentration (preferably, no more than 6%). When titanium dioxide having photocatalytic activity is irradiated with light, electrons and positive holes are generated, which react with the hydrogen peroxide to produce active oxygen. This active oxygen has a much more powerful oxidizing effect than ozone and is capable of oxidative decomposition of practically all organic substances to carbon dioxide. Even n-type semiconductor titanium oxide, which has a comparatively large band gap, for example, in the case where it is employed as a solution with aqueous hydrogen peroxide, easily generates active oxygen having a powerful oxidative effect on irradiation with light, as a result of which the values of charge dissociation, electron/hole mobility, and proton/hydroxyl group reaction are substantially raised compared with when this is employed on its own, producing a synergetic bleaching effect when combined with the oxidative action of the aqueous hydrogen peroxide itself. Thus, essentially, the photocatalytic function that can only be produced by irradiation with ultraviolet light of wavelength no more than 380 nm having energy corresponding to the band gap of titanium dioxide can be produced by irradiation with light produced by the system according to the present invention.

Next, in order to give a specific description of a system according to the present invention, systems incorporating various types of lamps were manufactured and tests were conducted. The test items and the results are shown in Table 1.

(1) Systems

Systems 1 to 11 incorporating various types of lamp and filter were employed for the system shown in FIG. 1.

(2) Test Method

Tests of bleaching of discolored teeth by application of the chemical agent and irradiation with light using systems 1 to 11 were conducted.

As the chemical agent, there was employed a solution obtained by mixing 0.5 g of titanium dioxide powder with 1 ml of 3% $H_2O_2$; this chemical agent was applied to the discolored teeth and the surfaces of the teeth, 1 mm in front of the end of the light-emitting section, were irradiated with light from emitting sections of systems 1 to 11.

(3) Light Source

In these tests, meta-halas (metal halide lamps) and halogens (halogen incandescent lamps) were employed as the light source. The details of the specifications of these are described below.

1) Metal Halide Lamps

Figure 2:
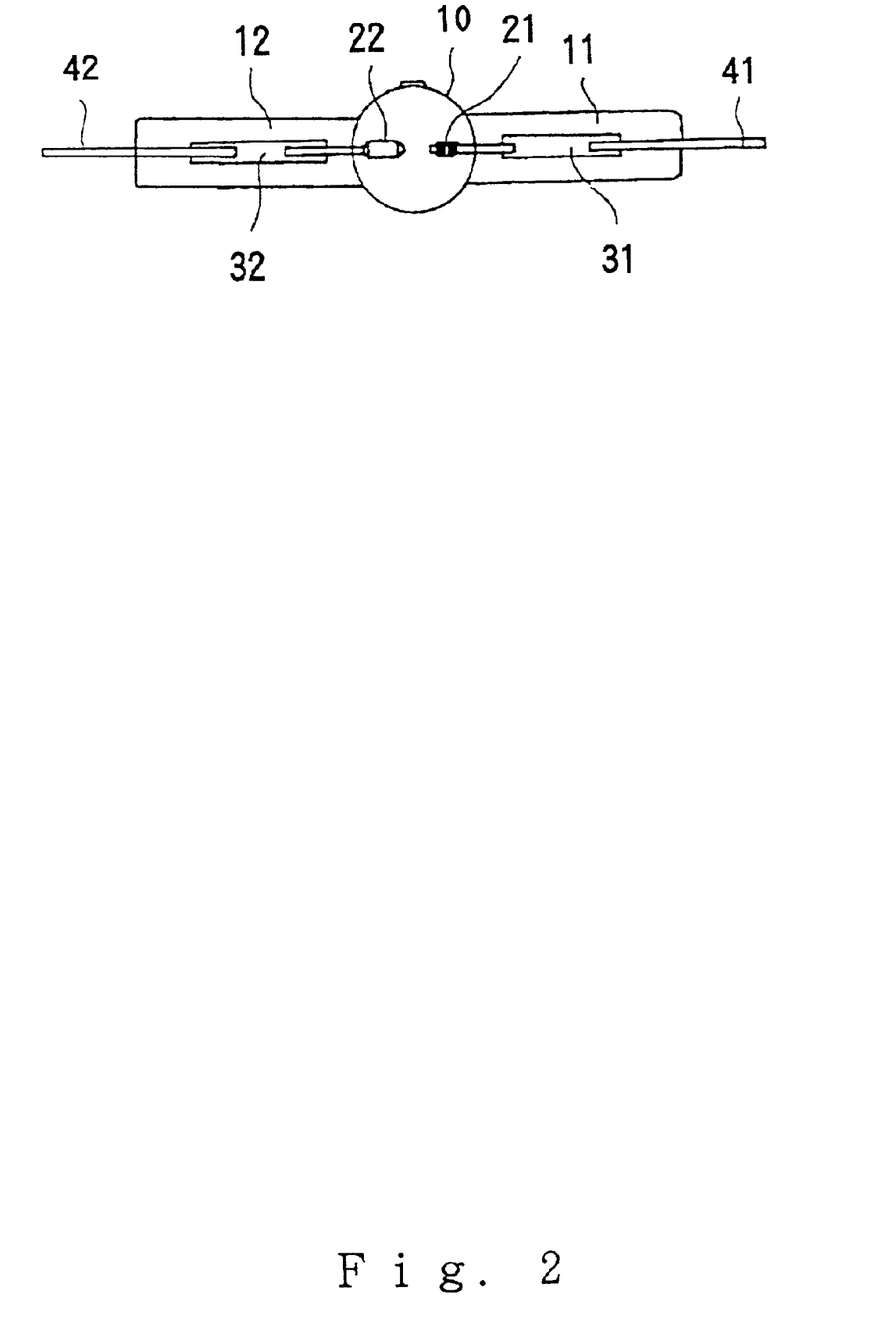
FIG. 2 is a diagram of a metal halide lamp employed as light source in the embodiment.

FIG. 2 is a diagram of a metal halide lamp; a light-emitting tube 10 made of quartz glass has an approximately spherical shape, with an maximum internal diameter of 9 mmø and an internal volume of 0.4 cc. Molybdenum foils 31 and 32 are respectively embedded in a sealed section 11 on the cathode side and a sealed section 12 on the anode side at both ends of light-emitting tube 10, cathode 21 and anode 22 base sections respectively connected to molybdenum foils 31 and 32 being arranged facing each other within light-emitting tube 10. An external inlet rod 41 on the cathode side with one end thereof welded to molybdenum foil 31 extends from the sealed section 11 on the cathode side and an external inlet rod 42 on the anode side with one end thereof welded to molybdenum foil 32 extends from the sealed section 12 on the anode side.

Mercury and argon constituting a rare gas for start-up are sealed within light-emitting tube 10. A halide of a light-emitting metal is sealed therein; as the light-emitting metal, in order to improve color rendering and the like, indium, dysprosium, holmium, erbium, thulium, cerium, praseodymium, neodymium, lutetium, gadolinium or cesium etc may be employed; as the halogen, iodine or bromine may be employed.

In the present tests, a device ignited with a rating of 70 V, 1.9 A having sealed therein 15.0 mg of mercury, 20 kPa of argon, 0.5 mg of dysprosium iodide and cesium iodide composite, 0.3 mg of mercury iodide and 0.1 mg of indium iodide was employed.

2) Halogen Incandescent Lamp

Figure 3:
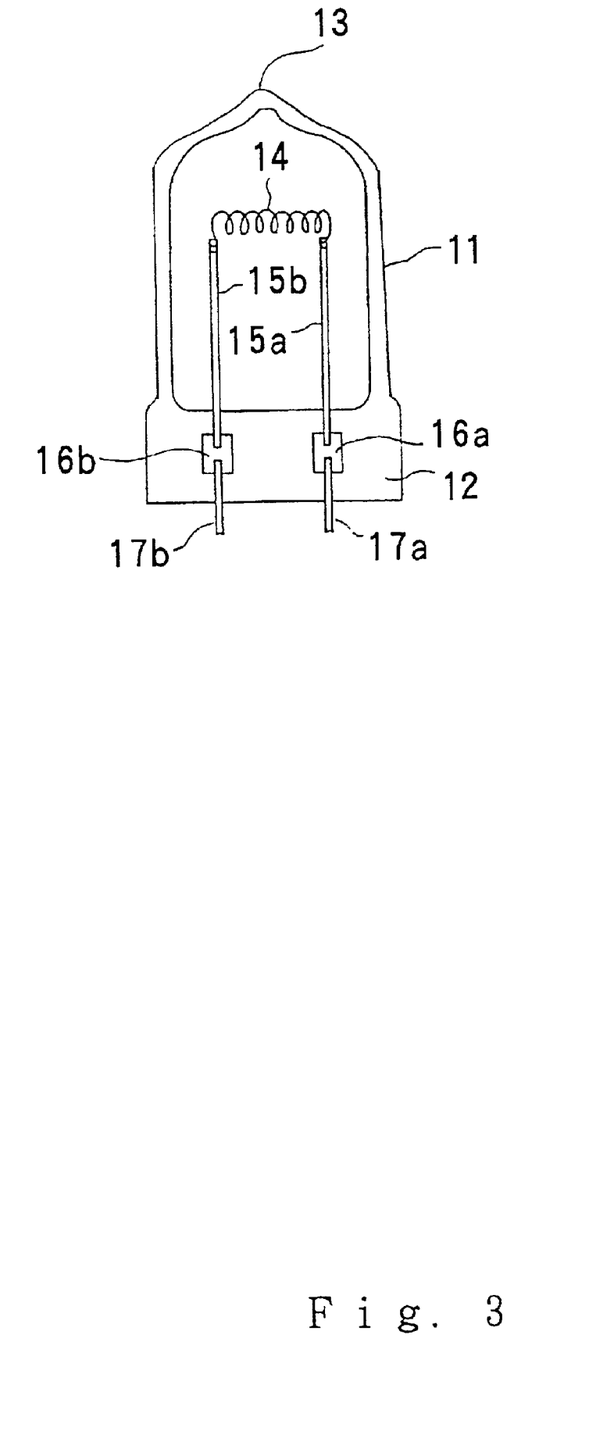
FIG. 3 is a diagram of a halogen incandescent lamp employed as light source in the embodiment.

FIG. 3 illustrates a halogen incandescent lamp. This has a sealed section 12 at one end formed with a gas-tight sealed section produced by pinch sealing, and at its other end has an exhaust tube residual section 13, comprising, for example, a bulb 11 made of hard glass, with a tungsten filament coil 14 arranged extending in a direction orthogonal to the tube axis of this bulb 11 within this bulb 11.

For example, inert gas and a halogen compound are sealed within bulb 11.

One internal lead rod 15a is connected with one end of filament coil 14 while another internal lead rod 15b is connected with the other end thereof. The tips of this one internal lead rod 15a and the other internal leader rod 15b respectively extend into sealed sections 12 and in these sealed sections 12 are connected with a pair of metal foils 16a and 16b which are embedded in mutually separated fashion. One external lead rod 17a and another external lead rod 17b extending to the outside from sealed sections 12 are respectively connected with respective metal foils 16a and 16b.

In these tests, a device ignited with a rating of 12 V, 8.3 A was employed.

Next, the details of systems 5, 6, 8 and 10 are described.

1) System 5

Figure 4:
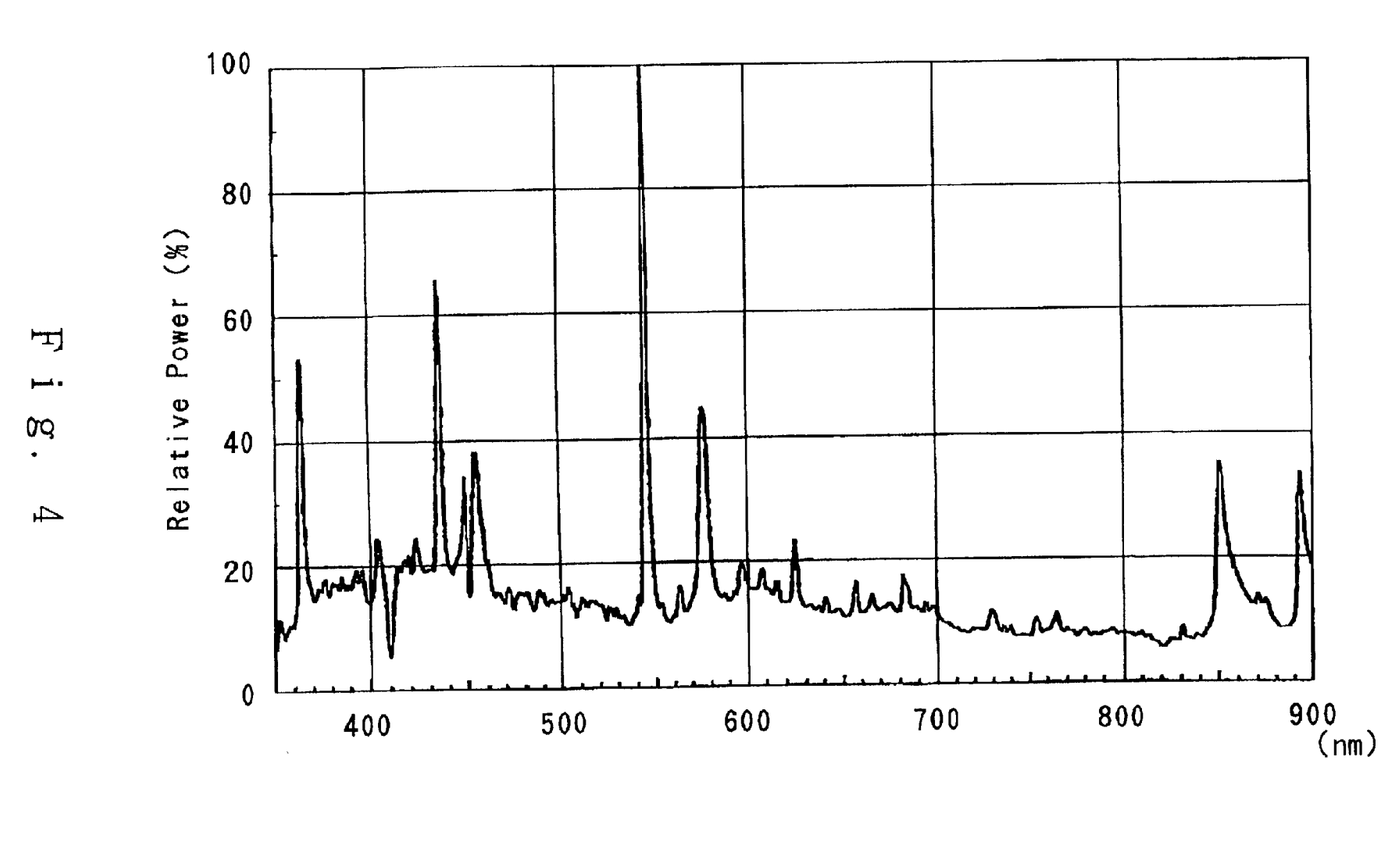
FIG. 4 is a spectral distribution diagram of the light source (metal halide lamp) unit of system 5.

FIG. 4 is a spectral distribution diagram of a discharge lamp (metal halide lamp) unit incorporated in system 5. In FIG. 4, the vertical axis indicates relative intensity.

Figure 5:
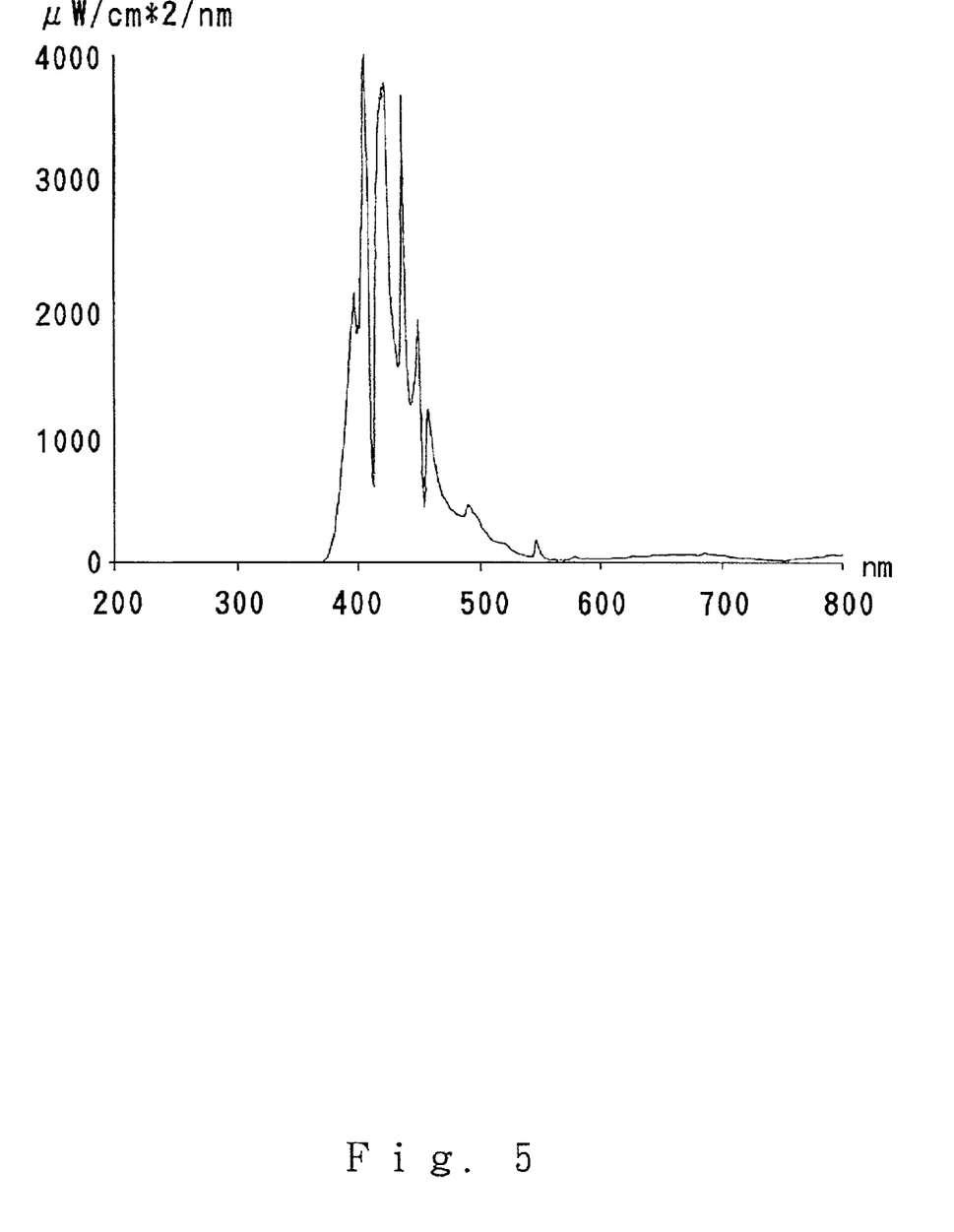
FIG. 5 is a spectral distribution diagram of the light emitted from the light-emitting section of system 5.

FIG. 5 is a spectral distribution diagram of the light emitted from the light-emitting section of system 5.

In this system, the following three filters were employed.

Filter 1: infra-red cut-off filter that cuts off above 800 nm;

Filter 2: cold filter that passes 200 to 450 nm; and

Filter 3: blue filter that passes wavelengths centered on 400 nm.

2) System 6

The spectral distribution diagram of the discharge lamp (metal halide lamp) unit incorporated in system 6 is the same as that of FIG. 4.

Figure 6:
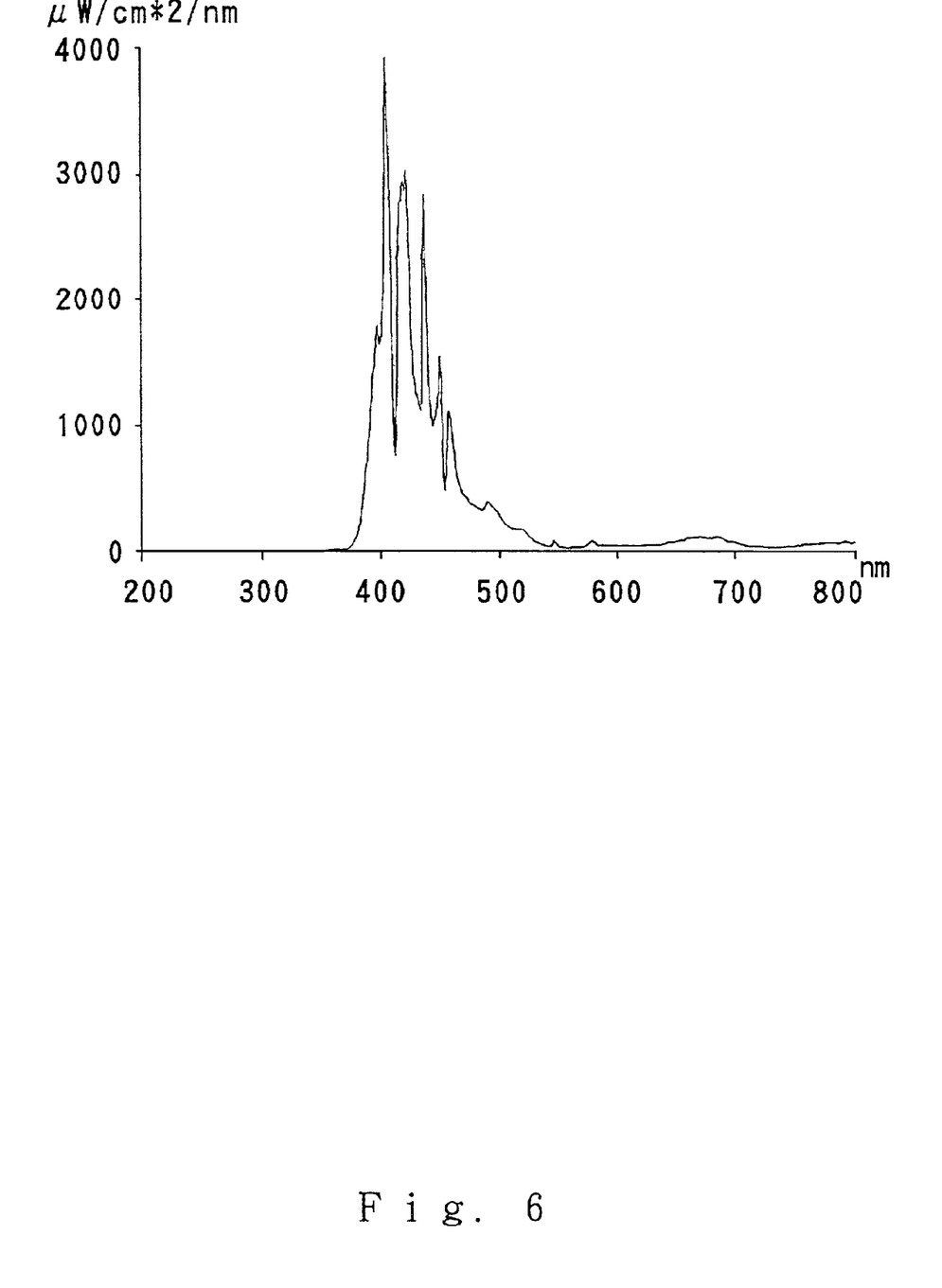
FIG. 6 is a spectral distribution diagram of the light emitted from the light-emitting section of system 6.

FIG. 6 shows a spectral distribution diagram of the light emitted from the light-emitting section of system 6.

TABLE 1

| | Light source | Irradiation energy of 380 to 420 nm (mW/cm$^2$) | Bleaching effect (irradiation time: 5 minutes) | % of irradiation energy of 380 to 420 nm/200 to 800 nm | Whether or not the temperature of the tooth pulp exceeds 40° C. (irradiation time: 5 minutes) | Percentage of irradiation energy of 380 nm or less/200 to 800 nm | Total results of evaluation |
|---|---|---|---|---|---|---|---|
| System 1 | Halogen | 44.8 | * | 18 | Exceeds | — | X |
| System 2 | Meta-hala | 29.6 | | — | — | — | X |
| System 3 | Meta-hala | 50.1 | ** | 17.6 | Exceeds | — | X |
| System 4 | Meta-hala | 47.8 | ** | 43.9 | Not Exceed | 28.6 | X |
| System 5 | Meta-hala | 72.9 | *** | 39.3 | Not Exceed | 0.8 | ○ |
| System 6 | Meta-hala | 64.7 | *** | 40.7 | Not Exceed | 0.5 | ○ |
| System 7 | Meta-hala | 37.5 | * | 22.5 | Exceeds | — | X |
| System 8 | Meta-hala | 87.1 | *** | 36.1 | Not Exceed | 0.5 | ○ |
| System 9 | Halogen | 46.8 | * | 27.4 | Exceeds | — | X |
| System 10 | Halogen | 55.6 | *** | 83.1 | Not Exceed | 3.1 | ○ |
| System 11 | Halogen | 64.1 | *** | 16.4 | Exceeds | — | X |
| | | 37 or more | | 36 or more | | Less than 5 | |

*: There exists the bleaching effect, and the degree thereof increases according as the number of asterisk increases.
X shows "no good" and ○ shows "good".

(4) Test Results

From the above test results, it was found that systems 5, 6, 8 and 10 satisfied all of the above conditions 1 and 2 and constituted the best discolored teeth bleaching devices.

Specifically, in systems 1 to 11, on examining the emission energy at 380 to 420 nm and the bleaching effect (irradiation time: five minutes), no bleaching effect was found in the case of system 2, which was less than 37 mW/cm$^2$.

Next, as a result of examining the ratio of irradiation energy of 380 to 420 nm with respect to the irradiation energy of 200 to 800 nm and whether or not the temperature of the pulp exceeded 40° C. (irradiation time: five minutes), it was found that, in the case of systems 4 to 6, 8 and 10, in which the ratio of irradiation energy of 380 to 420 nm, which contributes to the bleaching effect, was at least 36%, the temperature of the pulp did not exceed 40° C.

Further, as a result of an overall evaluation taking into account the fact that the ratio of irradiation energy of no more than 380 nm with respect to the irradiation energy of 200 to 800 nm or less is less than 5%, it was found that systems 5, 6, 8 and 10 constituted the best devices for bleaching discolored teeth.

In this system, the following three filters were employed.
Filter 1: infra-red cut-off filter that cuts off above 800 nm;
Filter 2: cold filter that passes 200 to 450 nm; and
Filter 3: blue filter that passes wavelengths centered on 400 nm.

3) System 8 spectral distribution diagram of the discharge lamp (metal halide lamp) unit incorporated in system 8 is the same as that of FIG. 4.

Figure 7:
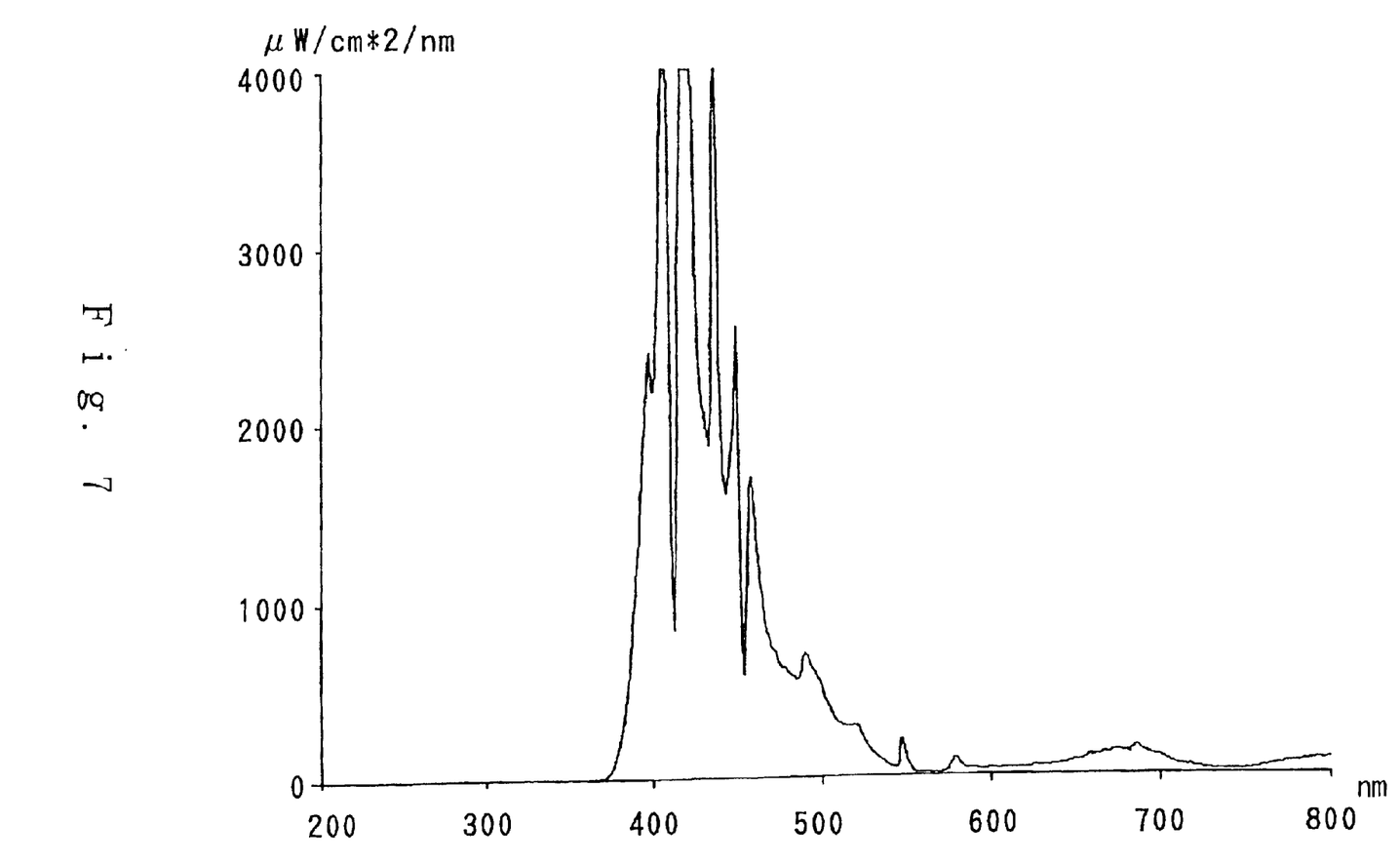
FIG. 7 is a spectral distribution diagram of the light emitted from the light-emitting section of system 8.

FIG. 7 shows a spectral distribution diagram of the light emitted from the light-emitting section of system 8.

In this system, the following filters were employed.
Filter 1: infra-red cut-off filter that cuts off above 800 nm;
Filter 2: cold filter that passes 200 to 450 nm; and
Filter 3: blue filter that passes wavelengths centered on 400 nm In system 5, system 6 and system 8, the light-guide member and the intensity of the light were varied, using the same lamp and same filter combination.

4) System 10

Figure 8:
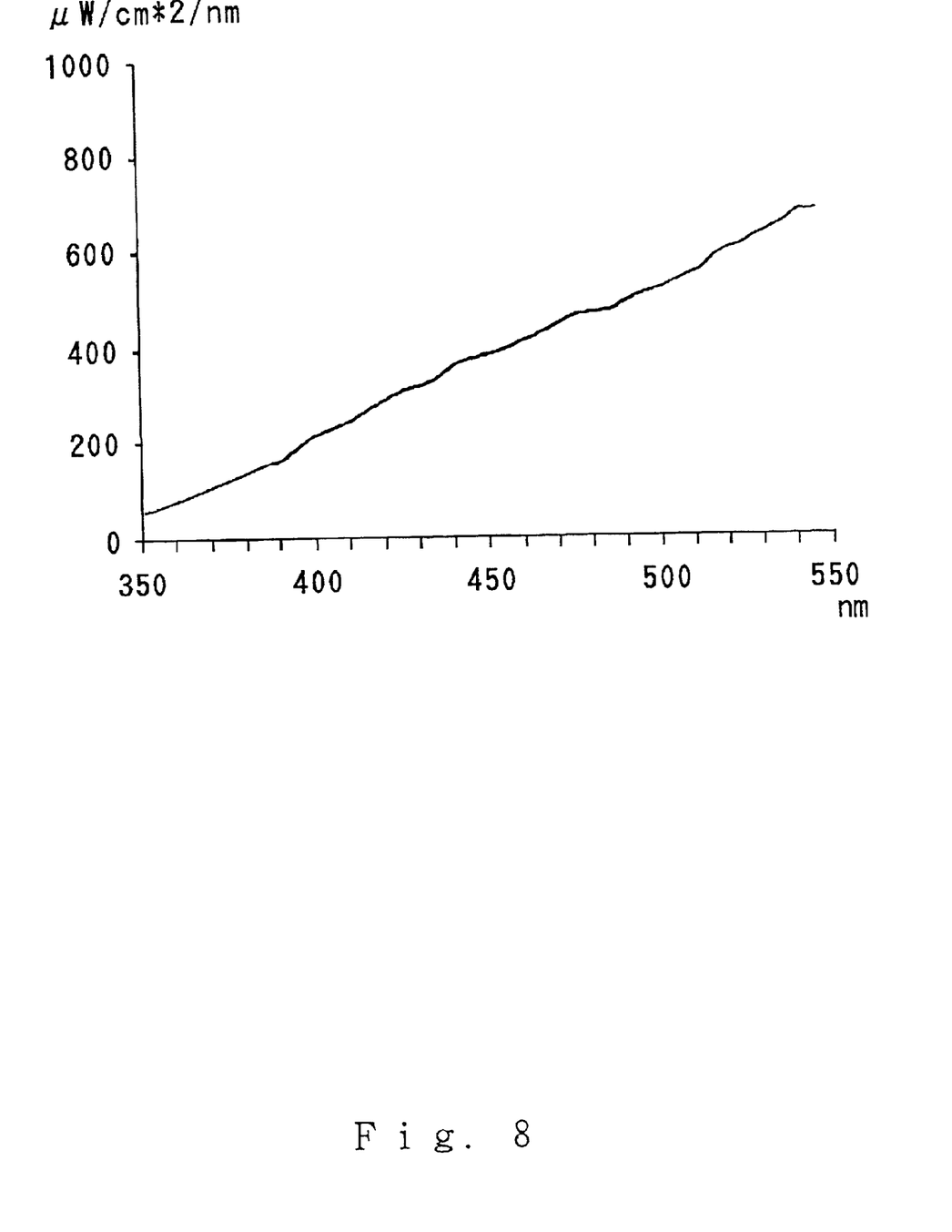
FIG. 8 is a spectral distribution diagram of a light source (halogen incandescent lamp) of system 10.

FIG. 8 is a spectral distribution diagram of an incandescent lamp (halogen lamp) unit incorporated in device 10.

Figure 9:
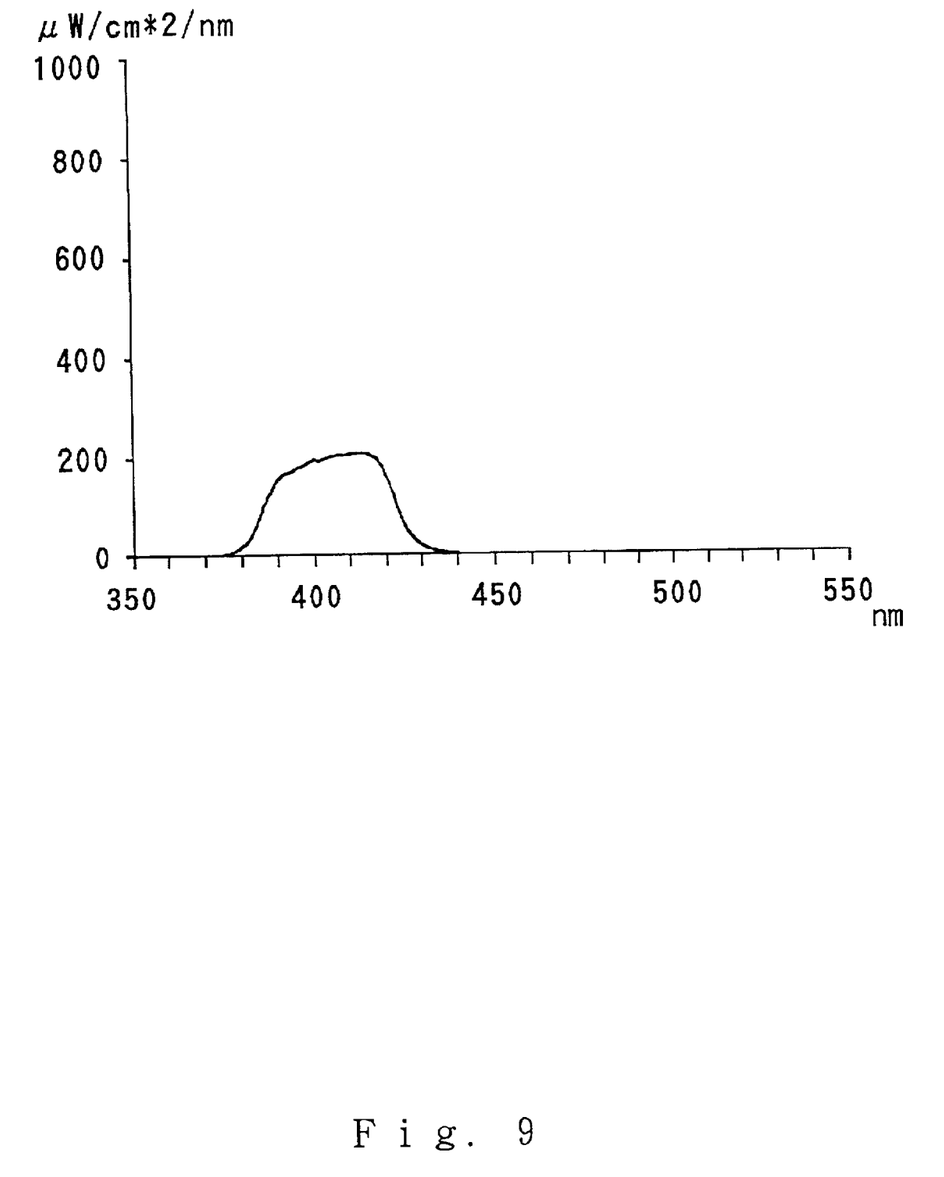
FIG. 9 is a spectral distribution diagram of the light emitted from the light-emitting section of system 10.

FIG. 9 is a spectral distribution diagram of the light emitted from the light-emitting section of system 10.

In this system, the following filter was employed:

wavelength selection filter that passes wavelengths in the region 380 to 420 nm but does not pass wavelengths other than these.

The following effects are obtained by the present invention.

(1) A system for bleaching discolored teeth can be provided, whereby an excellent bleaching effect can be obtained by irradiating with light the surface of teeth coated with a chemical agent comprising titanium dioxide and hydrogen peroxide.

(2) A high bleaching effect with an irradiating time of no more than five minutes can be obtained by irradiation with light using the system of the present invention.

(3) The temperature of the pulp does not exceed 40° C. (reference time: five minutes).

(4) The irradiation energy of no more than 380 nm represents less than 5% of the irradiation energy of 200 to 800 nm, so there is no risk of an adverse effect on the human body.

(5) It is useful as a system for irradiation with light used for bleaching of discolored teeth using a chemical agent comprising titanium dioxide and low-concentration (no more than 6%) hydrogen peroxide.

(6) The system of the present invention has the distinct advantages that a high degree of bleaching effect of the teeth can be achieved with little heat being supplied to the teeth (less than 40° C.) and emission of ultraviolet radiation, which has an adverse effect on the human body, can be reduced to a low level.

What is claimed is:

1. An apparatus for bleaching discolored teeth, which comprises:

a light source, a mirror for condensing the light from said light source, a wavelength cut-off filter and a light-emitting section, wherein the light emitted from the light-emitting section having a wavelength of 800 nm or higher is cut from the spectrum of light emitted by the light-emitting section by the wavelength cut-off filter, the radiant energy of light of the wavelength range of 380 to 420 nm is at least 37 mW/cm$^2$, and the ratio of radiant energy of light within the wavelength range of 380 to 420 nm to radiant energy of light within the wavelength range of 200 to 800 nm is at least 36% of the light emitted from the light-emitting section.

2. The apparatus for bleaching discolored teeth according to claim 1, wherein the apparatus further comprises a light-guide member, a component of which at the tip of the light-guide member is said light-emitting section.

3. The apparatus for bleaching discolored teeth according to claim 1, wherein the light-guide member is an optical fiber.

4. The apparatus for bleaching discolored teeth according to claim 1, wherein the wavelength cut-off filter is a single filter or a plurality of filters selected from the group consisting of an infra-red cut-off filter that cuts-off light of wavelengths of 800 nm and greater, a cold filter that passes wavelengths of light in the region of 200 to 450 nm, a blue filter that passes wavelengths of light centered at 400 nm and a wavelength selection filter that passes wavelengths of the region 380 to 420 nm, but does not pass light of other wavelengths.

* * * * *